(12) United States Patent
Urban et al.

(10) Patent No.: US 11,401,542 B2
(45) Date of Patent: Aug. 2, 2022

(54) ACOUSTICALLY ACTUATED DROPLET APPARATUS AND A CHEMICAL ANALYSIS METHOD BY USING ACOUSTICALLY ACTUATED DROPLET

(71) Applicant: National Tsing Hua University, Hsinchu (TW)

(72) Inventors: Pawel Lukasz Urban, Hsinchu (TW); Tzu-Hsien Yang, New Taipei (TW)

(73) Assignee: National Tsing Hua University, Hsinchu (TW)

( * ) Notice: Subject to any disclaimer, the term of this patent is extended or adjusted under 35 U.S.C. 154(b) by 324 days.

(21) Appl. No.: 16/660,881

(22) Filed: Oct. 23, 2019

(65) Prior Publication Data
US 2021/0123088 A1    Apr. 29, 2021

(51) Int. Cl.
*C12Q 1/34*    (2006.01)
*B01L 3/00*    (2006.01)
*B01F 31/80*   (2022.01)

(52) U.S. Cl.
CPC ............... *C12Q 1/34* (2013.01); *B01F 31/84* (2022.01); *B01L 3/502761* (2013.01); *B01L 2400/0436* (2013.01)

(58) Field of Classification Search
CPC ............. B01L 3/5027; B01L 3/502761; B01L 2400/0436; C12Q 1/34; B01F 31/84
See application file for complete search history.

(56) References Cited

U.S. PATENT DOCUMENTS 6,216,538 B1 *    4/2001  Yasuda ................. G10K 15/00
                                                73/570.5
2020/0276579 A1 *  9/2020  Huang ..................... B01F 31/87
(Continued)

FOREIGN PATENT DOCUMENTS

WO    WO 2014029505 A1    2/2014
WO    WO 2015107014 A1    7/2015

OTHER PUBLICATIONS

Cohen et al., "UV-Vis Absorbance Spectroscopy in Single Acoustically Levitated Droplets as a Tool to Study Atmospheric Chemistry in Real Time", American Geophysical Union, Fall Meeting 2018, dated on Dec. 10-14, 2018, Poster, United States.
(Continued)

*Primary Examiner* — Brian J. Sines
(74) *Attorney, Agent, or Firm* — Fay Sharpe LLP (57) ABSTRACT

An acoustically actuated droplet apparatus includes a first sound source, a second sound source, a thread, two fixed columns and at least one droplet transporter. The first sound source includes a first emitting surface. The second sound source includes a second emitting surface, wherein the second emitting surface and the first emitting surface are arranged opposite to each other. The thread is coaxially passed through and placed between the first sound source and the second sound source, wherein the thread is hydrophobic. The two fixed columns are connected to two ends of the thread, wherein the first sound source and the second sound source are placed between the two fixed columns. The droplet transporter includes a tubing, a droplet dispenser and a solution container, wherein the droplet dispenser is connected with the solution container by the tubing, and the droplet dispenser is placed near the thread.

6 Claims, 12 Drawing Sheets

(56) References Cited

U.S. PATENT DOCUMENTS

2021/0039128 A1\* 2/2021 Bowen ................ B01J 19/0046
2021/0101148 A1\* 4/2021 Lal ....................... F04B 19/006

OTHER PUBLICATIONS

Crawford et al., "Real Time Monitoring of Containerless Microreactions in Acoustically Levitated Droplets via Ambient Ionization Mass Spectrometry", analytical chemistry, published on Sep. 6, 2016, vol. 88, issue 17, pp. 8396-8403, published by American Chemical Society, United States.

Marzo et al., "TinyLev: A multi-emitter single-axis acoustic levitator", Review of Scientific Instruments, published in Aug. 2017, vol. 88, issue 8, pp. 085105-1-085105-6, published by American Institute of Physics, United States.

Santesson et al., "Airborne Cell Analysis", analytical chemistry, published on Aug. 1, 2000, vol. 72, issue 15, pp. 3412-3418, published by American Chemical Society, United States.

Santesson et al., "Airborne chemistry: acoustic levitation in chemical analysis", Analytical and Bioanalytical Chemistry, published in Apr. 2004, vol. 378, issue 7, pp. 1704-1709, published by Springer-Verlag, Germany.

\* cited by examiner

ACOUSTICALLY ACTUATED DROPLET APPARATUS AND A CHEMICAL ANALYSIS METHOD BY USING ACOUSTICALLY ACTUATED DROPLET

BACKGROUND

Technical Field

The present disclosure relates to an acoustically actuated droplet apparatus and a chemical analysis method by using acoustically actuated droplet. More particularly, the present disclosure relates to an acoustically actuated droplet apparatus and a chemical analysis method by using acoustically actuated droplet with an acoustic levitation technology.

Description of Related Art

In the conventional fluorometric assays, samples with the volumes of 2 to 3 mL are normally used in order to fill up the quartz cuvette, and enable excitation of fluorophore. However, some types of samples are limited in volume, and a chemical reaction is often performed before the fluorometric detection. The reagents provided to the chemical reaction are often expensive. Hence, it is necessary to decrease the volumes of both sample and reagent in fluorometric assays.

Currently, microtiter plates are usually used to downscale chemical assays. In this case, the sample volume is approximately in the order of tens of microliters, and the sample and the reagent are mixed by manual or robotic pipetting. In addition, various types of microfluidic devices are used for analyzing microscale samples. However, those devices are normally fabricated in specialized facilities and are costly.

However, mixing sample with reagent in the microscale environment is a considerable problem. The liquid flow in the microfluidic channels is dominated by laminar flow. Various chip designs have been proposed to increase turbulence in the microfluidic channels. Furthermore, in the absence of turbulence, the sample and the reagent can be mixed by diffusion. For diffusion to play a role in mixing, the surface-to-volume ratio of a liquid aliquot has to be minimized. The geometrical figure with the lowest surface-to-volume ratio is sphere. The shape of liquid droplets suspended in the air is similar to the sphere. However, the available methods for analysis and detection of droplet suspended in the air are scarce, and have limited practicality.

Therefore, how to develop an analysis instrument for the microscale samples, which can analyze the liquid sample in the microliter range, is the goal of the relevant industry.

SUMMARY

According to one aspect of the present disclosure, an acoustically actuated droplet apparatus is provided. The acoustically actuated droplet apparatus includes a first sound source, a second sound source, a thread, two fixed columns and at least one droplet transporter. The first sound source includes a first emitting surface. The second sound source includes a second emitting surface, wherein the second emitting surface and the first emitting surface are arranged opposite to each other. The thread is coaxially passed through and placed between the first sound source and the second sound source, wherein the thread is hydrophobic. The two fixed columns are connected to two ends of the thread, wherein the first sound source and the second sound source are placed between the two fixed columns. The droplet transporter includes a tubing, a droplet dispenser and a solution container, wherein the droplet dispenser is connected with the solution container by the tubing, and the droplet dispenser is placed near the thread.

According to another aspect of the present disclosure, a chemical analysis method by using acoustically actuated droplet includes steps as follows. An acoustically actuated droplet apparatus is provided, wherein the acoustically actuated droplet apparatus includes a first sound source, a second sound source, a thread, two fixed columns, at least two droplet transporters and a detection device. The first sound source includes a first emitting surface. The second sound source includes a second emitting surface, wherein the second emitting surface and the first emitting surface are arranged opposite to each other. The thread is coaxially passed through and placed between the first sound source and the second sound source, wherein the thread is hydrophobic. The two fixed columns are connected to two ends of the thread, wherein the first sound source and the second sound source are placed between the two fixed columns. The at least two droplet transporters, each of the at least two droplet transporters includes a tubing, a droplet dispenser and a solution container, wherein the droplet dispenser is connected with the solution container by the tubing, and the droplet dispenser is placed near the thread. The detection device is biased toward the second sound source, wherein the detection device is located on one side of the thread. A leading droplet is provided, wherein the leading droplet is transported to the thread by one of the at least two droplet transporters. A leading droplet moving step is performed, wherein an intensity of sound wave of the second sound source is decreased, so that the leading droplet is moved to the second sound source. At least one droplet is provided, wherein the at least one droplet is transported to the thread by the other of the at least two droplet transporters. A droplet moving step is performed, wherein the at least one droplet and the leading droplet are moved to the second sound source. A droplet merging step is performed, wherein the at least one droplet and the leading droplet are merged into a testing droplet. A detection step is performed, wherein the testing droplet is transported to a detecting region, and the detecting region is corresponding to the detection device, so as to detect the testing droplet.

BRIEF DESCRIPTION OF THE DRAWINGS

The present disclosure can be more fully understood by reading the following detailed description of the embodiment, with reference made to the accompanying drawings as follows.

DETAILED DESCRIPTION

The embodiments of the present disclosure will be described below by referring the figures. For the clarity, many practical details will be explained in the following description. However, the readers should realize that these practical details are not limited to the present disclosure. That is, in some embodiments of the present disclosure, the practical details are not necessary. In addition, in order to simplify the figures, some of the conventional structures and elements will be shown in the figures with simplified schematic; and the repeated elements will be shown by the same reference numerals.

Figure 1:
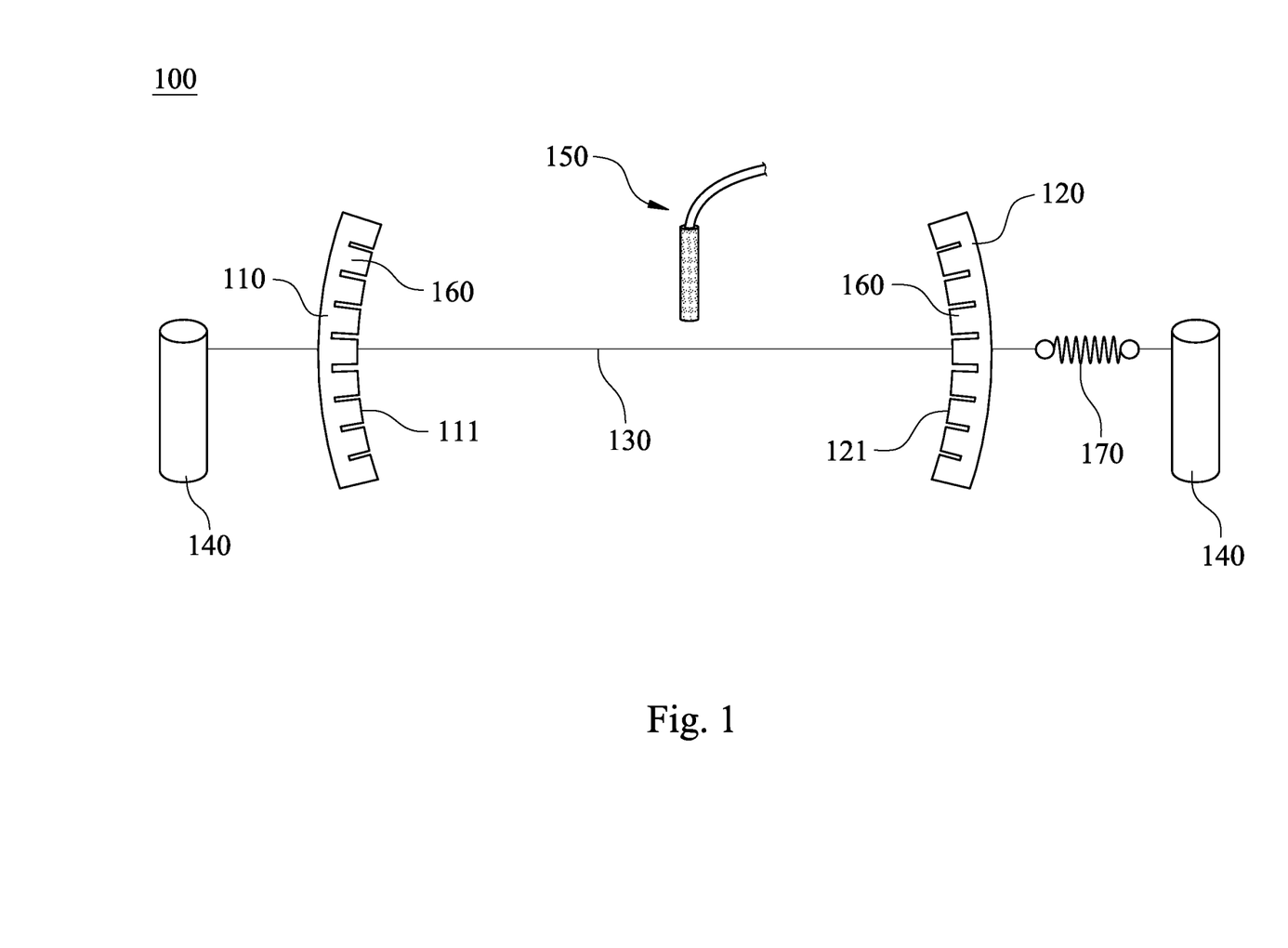
FIG. 1 is a schematic diagram of an acoustically actuated droplet apparatus according to one embodiment of the present disclosure.

Please refer to FIG. 1, which is a schematic diagram of an acoustically actuated droplet apparatus 100 according to one embodiment of the present disclosure. As shown in FIG. 1, the acoustically actuated droplet apparatus 100 includes a first sound source 110, a second sound source 120, a thread 130, two fixed columns 140 and at least one droplet transporter 150.

Specifically, the first sound source 110 includes a first emitting surface 111, the second sound source 120 includes a second emitting surface 121, wherein the second emitting surface 121 and the first emitting surface 111 are arranged opposite to each other. The thread 130 is coaxially passed through and placed between the first sound source 110 and the second sound source 120. The two fixed columns 140 are connected to two ends of the thread 130, wherein the first sound source 110 and the second sound source 120 are placed between the two fixed columns 140.

In the embodiment of FIG. 1, the first emitting surface 111 and the second emitting surface 121 can be concave structures, and are provided with a plurality of sound transducers 160, wherein the sound transducers 160 are arranged in an array. Specifically, the first emitting surface 111 of the first sound source 110 and the second emitting surface 121 of the second sound source 120 emit sound waves. The two sound waves produce a standing wave. The concave structures of the first emitting surface 111 and the second emitting surface 121 have a focusing effect on the standing wave, which can improve the suspension capability of the standing wave. Furthermore, the thread 130 is hydrophobic, and made of a chemically inert hydrophobic material. More preferably, the thread 130 can be but is not limited to a polytetrafluoroethene thread. By introducing the thread 130, the droplet transported from the droplet transporter 150 can be guided by the standing wave between the first sound source 110 and the second sound source 120 in a reliable manner. The thread 130 stabilizes droplet movement at a relatively low power of the emitted sound. The acoustically actuated droplet apparatus 100 of the present disclosure can further include an extension spring 170, wherein the extension spring 170 is connected between one end of the thread 130 and one of the two fixed columns 140 for tensioning and adjusting the tension of the thread 130.

Figure 2:
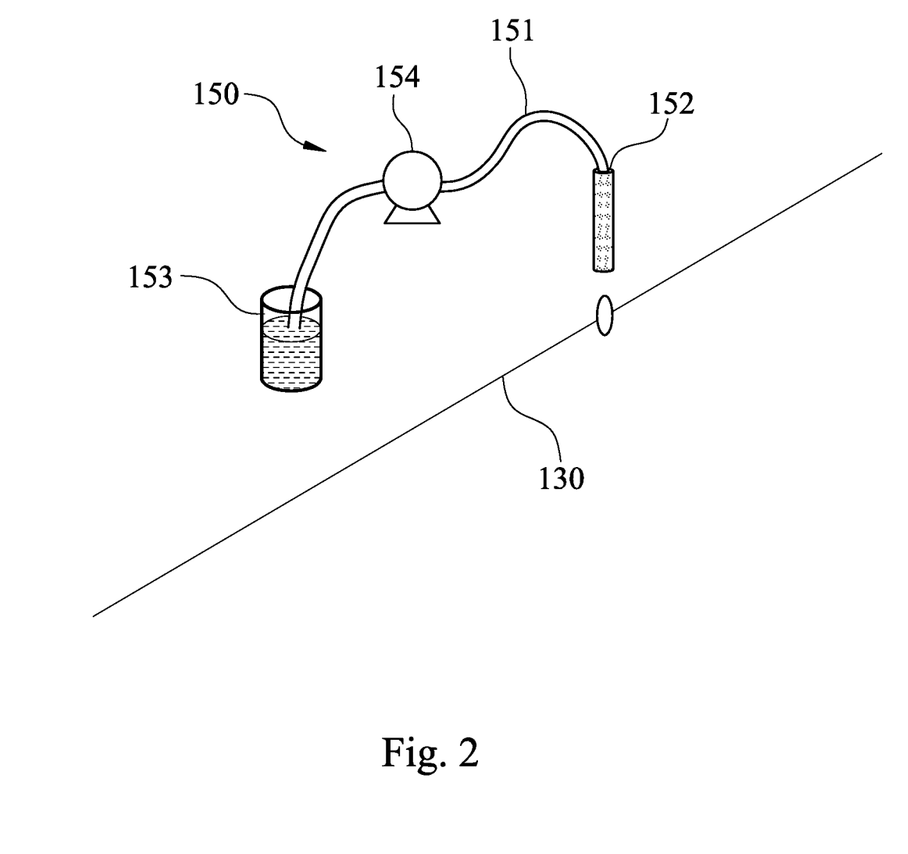
FIG. 2 is a schematic diagram of the droplet transporter as shown in FIG. 1.

Please refer to FIG. 2, which is a schematic diagram of the droplet transporter 150 as shown in FIG. 1. Specifically, the droplet transporter 150 includes a tubing 151, a droplet dispenser 152 and a solution container 153. The droplet dispenser 152 is connected with the solution container 153 by the tubing 151, and the droplet dispenser 152 is placed near the thread 130. Furthermore, the droplet transporter 150 can further include a peristatic pump 154. The tubing 151 is connected to the solution container 153 via the peristatic pump 154, and the peristatic pump 154 is for driving the solution in the solution container 153 to the droplet dispenser 152. That is, the droplet delivered to the thread 130 by the droplet transporter 150 is the solution in the solution container 153 driven by the peristatic pump 154 and transported to the droplet dispenser 152 via the tubing 151. Then, the droplet is dropped on the thread 130 by the droplet dispenser 152.

Therefore, the acoustically actuated droplet apparatus of the present disclosure is using the standing wave generated between the first sound source and the second sound source to fix the droplet on the thread, and the droplet is transported by the droplet transporter. Furthermore, by changing the intensity of the sound wave of one of the sound sources, the resulting sound intensity gradient breaks the equilibrium state of the actuated droplet, so that the droplet is pushed towards the weaker sound source to achieve the transport of droplet. The distance of the droplet actuation is related to the droplet size, that is, the larger the droplet, the farther it can be transported.

Figure 3:
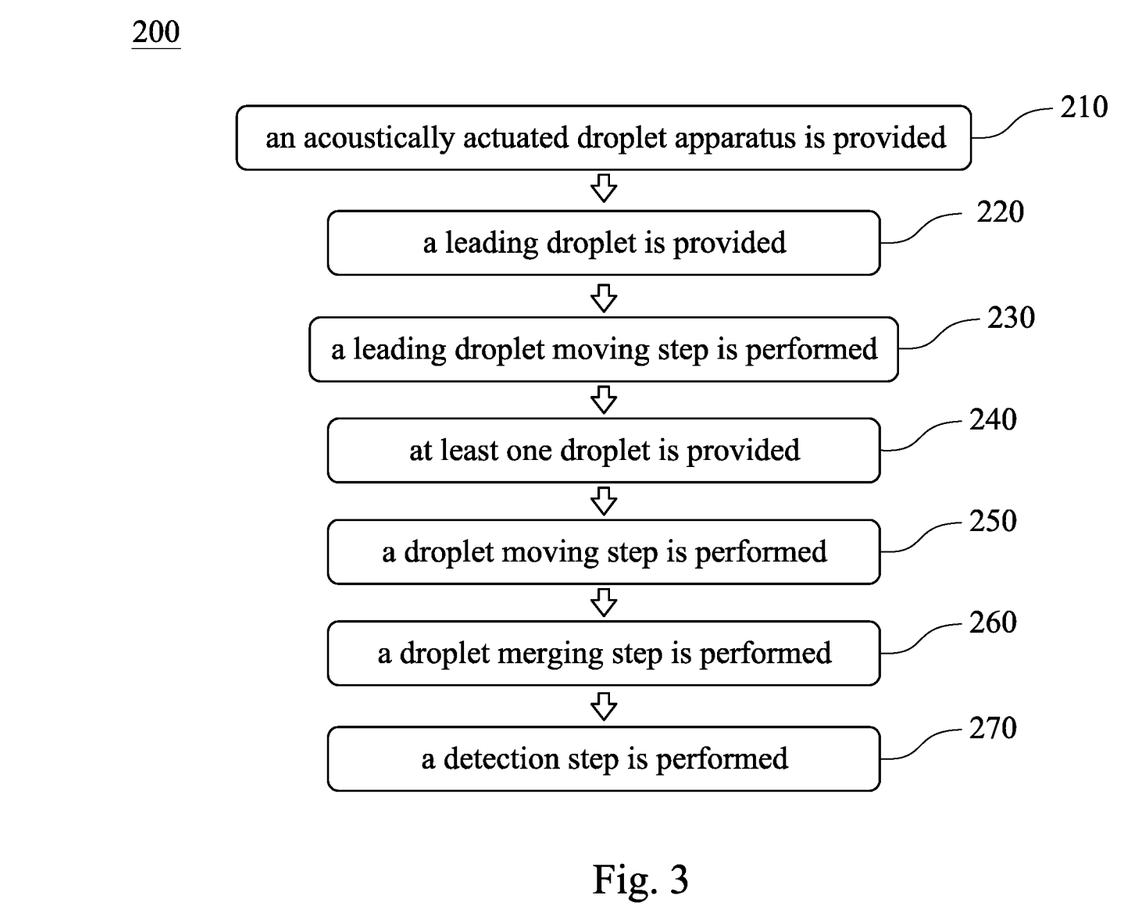
FIG. 3 is a flow chart of a chemical analysis method by using acoustically actuated droplet according to another embodiment of the present disclosure.
Figure 4:
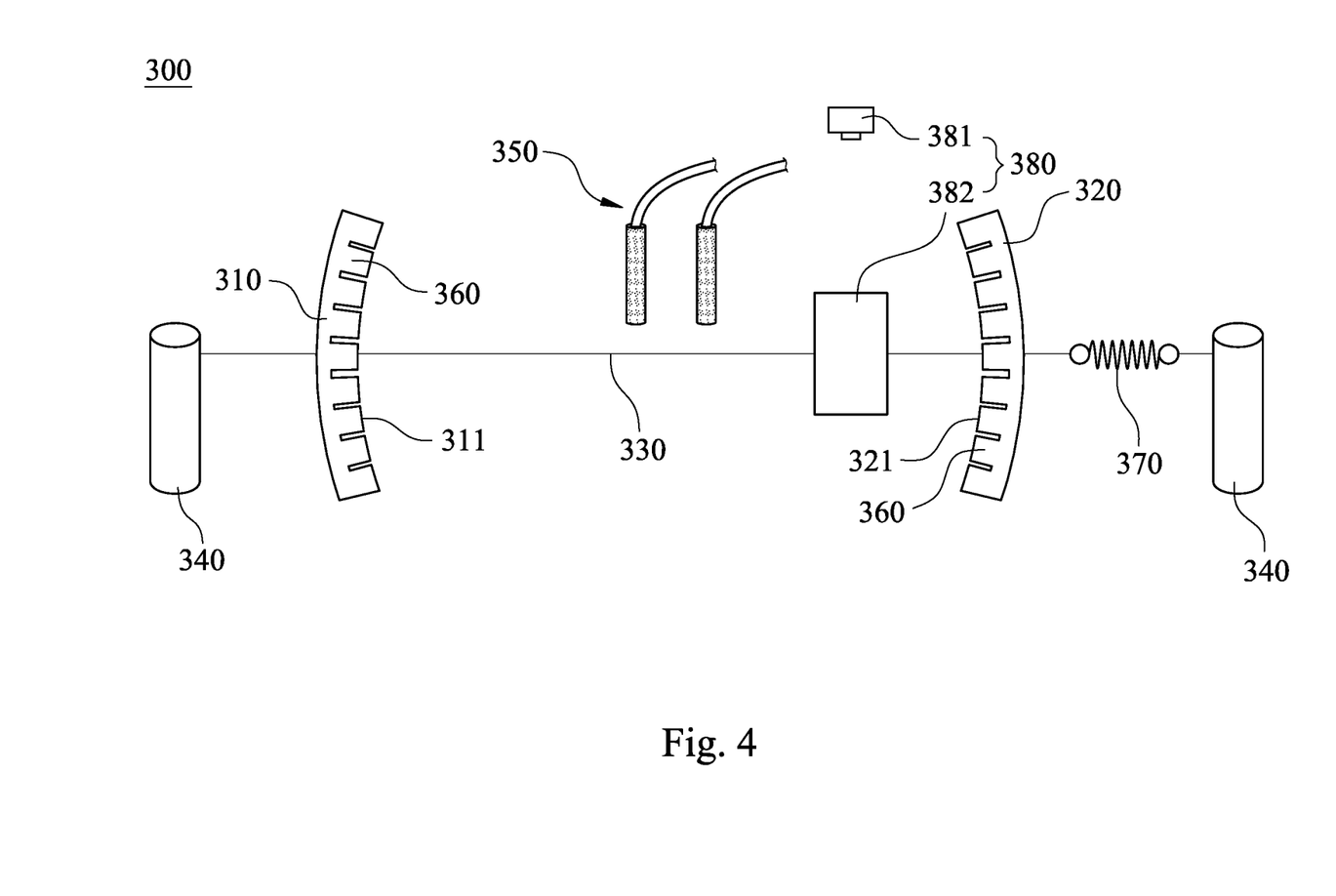
FIG. 4 is a schematic diagram of an acoustically actuated droplet apparatus as shown in FIG. 3.

Please refer to FIG. 3 and FIG. 4. FIG. 3 is a flow chart of a chemical analysis method by using acoustically actuated droplet 200 according to another embodiment of the present disclosure. FIG. 4 is a schematic diagram of an acoustically actuated droplet apparatus 300 as shown in FIG. 3. The chemical analysis method by using acoustically actuated droplet 200 includes a step 210, a step 220, a step 230, a step 240, a step 250, a step 260 and a step 270.

In the step 210, an acoustically actuated droplet apparatus 300 is provided, as shown in FIG. 4. The acoustically actuated droplet apparatus 300 includes a first sound source 310, a second sound source 320, a thread 330, two fixed columns 340, at least two droplet transporters 350, and a detection device 380. Specifically, the first sound source 310 includes a first emitting surface 311, the second sound source 320 includes a second emitting surface 321, wherein the second emitting surface 321 and the first emitting surface 311 are arranged opposite to each other. The thread 330 is coaxially passed through and placed between the first sound source 310 and the second sound source 320. The two fixed columns 340 are connected to two ends of the thread 330, wherein the first sound source 310 and the second sound source 320 are placed between the two fixed columns 340.

In the embodiment of FIG. 4, the first emitting surface 311 and the second emitting surface 321 can be concave structures, and are provided with a plurality of sound transducers 360, wherein the sound transducers 360 are arranged in an array. Specifically, the first emitting surface 311 of the first sound source 310 and the second emitting surface 321 of the second sound source 320 emit sound waves. The two sound waves produce a standing wave. The concave structures of the first emitting surface 311 and the second emitting surface 321 have a focusing effect on the standing wave, which can improve the suspension capability of the standing wave. Furthermore, the thread 330 is hydrophobic, and made of a chemically inert hydrophobic material. More preferably, the thread 330 can be but is not limited to a polytetrafluoroethene thread. By introducing the thread 330, the droplet transported from the droplet transporter 350 can be guided by the standing wave between the first sound source 310 and the second sound source 320 in a reliable manner. The thread 330 stabilizes droplet movement at a relatively low power of the emitted sound. The acoustically actuated droplet apparatus 300 of the present disclosure can further include an extension spring 370, wherein the extension spring 370 is connected between one end of the thread 330 and one of the two fixed columns 340 for tensioning and adjusting the tension of the thread 330.

Figure 5:
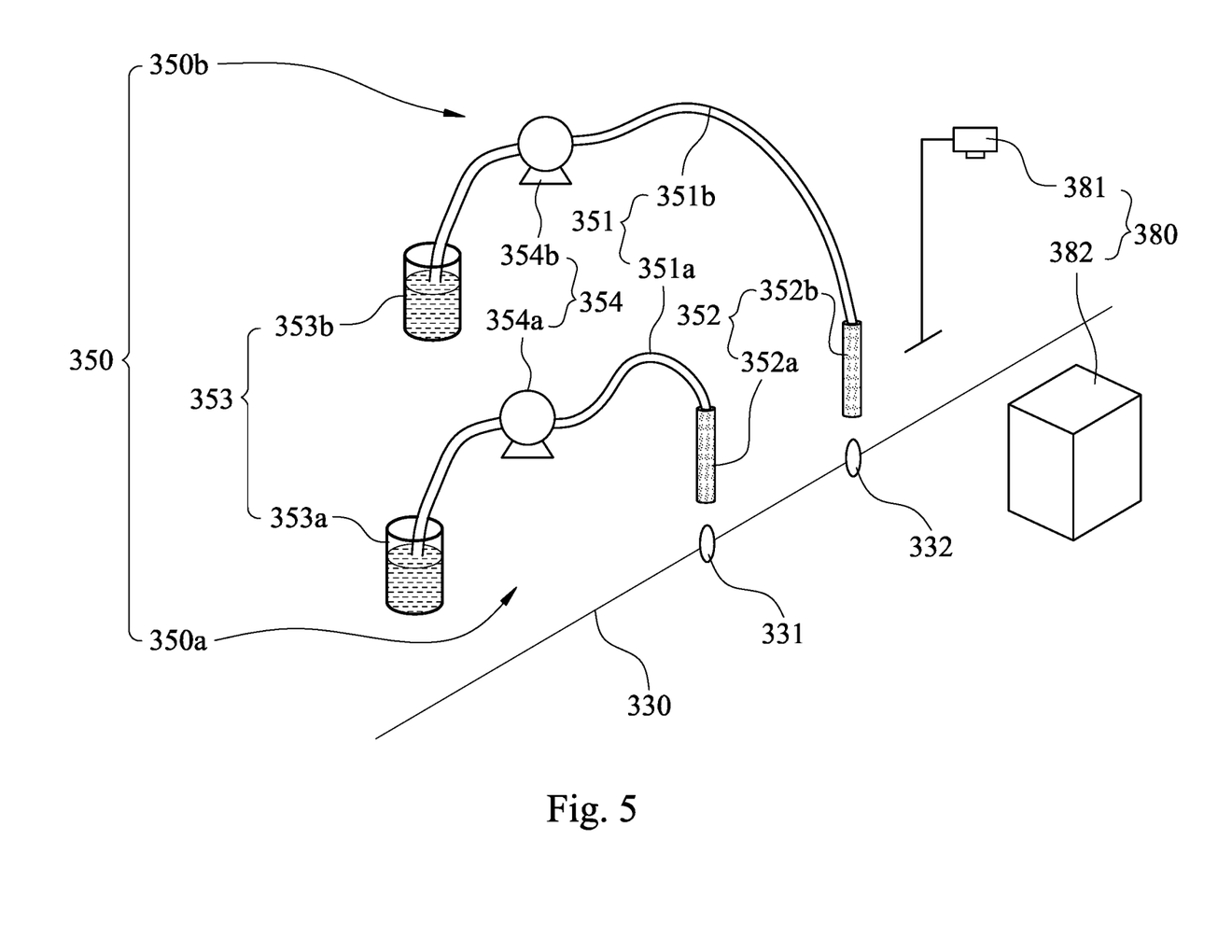
FIG. 5 is a partial schematic diagram of the acoustically actuated droplet apparatus as shown in FIG. 4.

Please refer to FIG. 5, which is a partial schematic diagram of the acoustically actuated droplet apparatus 300 as shown in FIG. 4. Specifically, each of the at least two droplet transporters 350 includes a tubing 351, a droplet dispenser 352, and a solution container 353. The droplet dispenser 352 is connected with the solution container 353 by the tubing 351, and the droplet dispenser 352 is placed near the thread 330. Furthermore, each of the at least two droplet transporters 350 can further include a peristatic pump 354. The tubing 351 is connected to the solution container 353 via the peristatic pump 354, and the peristatic pump 354 is for driving the solution in the solution container 353 to the droplet dispenser 352. That is, the droplet delivered to the thread 330 by the droplet transporter 350 is the solution in the solution container 353 driven by the peristatic pump 354 and transported to the droplet dispenser 352 via the tubing 351. Then, the droplet is dropped on the thread 330 by the droplet dispenser 352.

The technique according to the present disclosure enables the chemical reaction by merging the droplets. Therefore, at least two droplets should be dispensed, one containing the sample and one containing the reagent. In the embodiment of FIG. 4 and FIG. 5, a number of the droplet transporter is two, which are a first droplet transporter 350a and a second droplet transporter 350b, respectively. The first droplet transporter 350a is corresponding to a first solution container 353a, and the second droplet transporter 350b is corresponding to a second solution container 353b. The first solution container 353a and the second solution container 353b are separately for accommodating the different solutions, and the different solutions can react with each other. That is, one of the two different solutions is a sample solution, and the other is a reagent solution which can react with the sample solution. According to the present disclosure, the first solution container 353a accommodates a leading solution, and the leading solution is the sample solution.

Figure 6A:
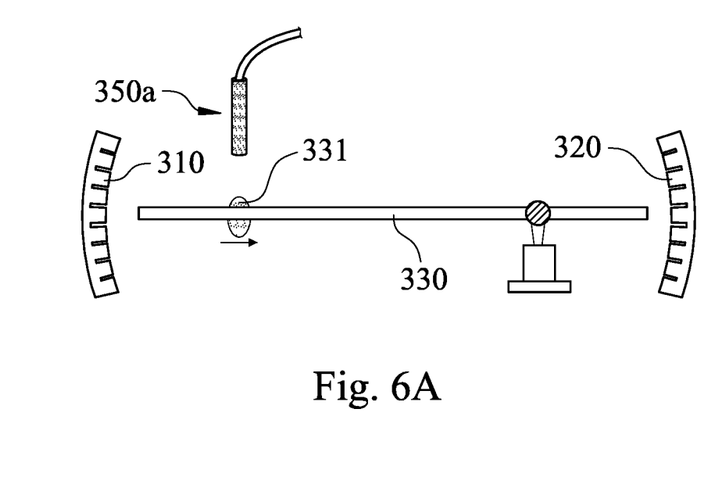
FIGS. 6A, 6B, 6C, 6D, 6E and 6F are process diagrams of the chemical analysis method by using acoustically actuated droplet as shown in FIG. 3.
Figure 6B:
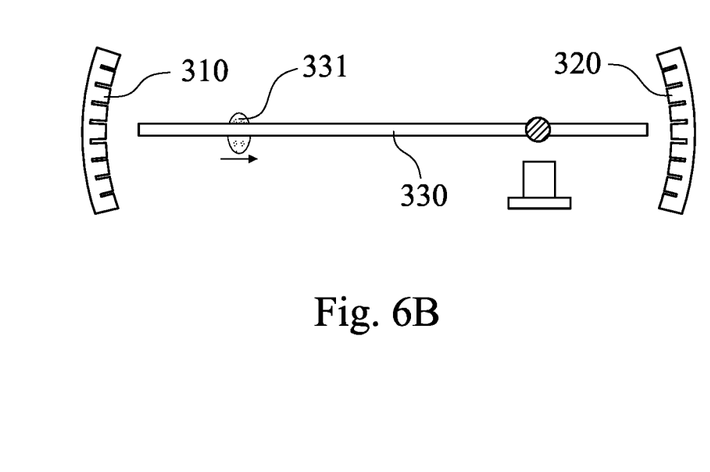
Figure 6C:
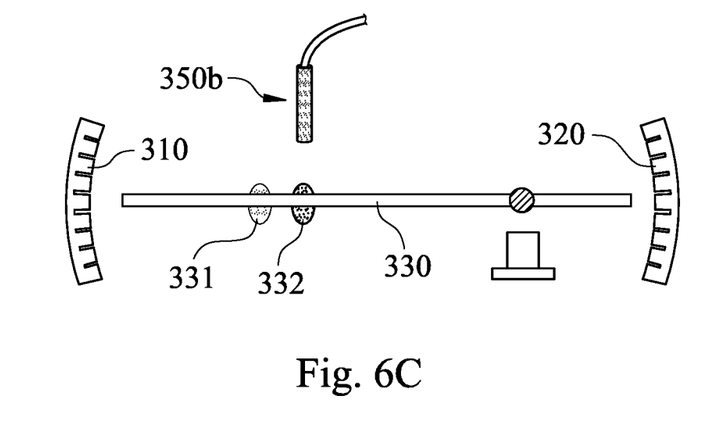
Figure 6D:
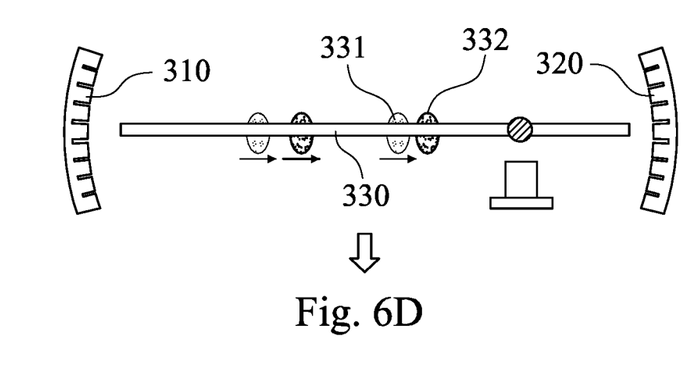
Figure 6E:
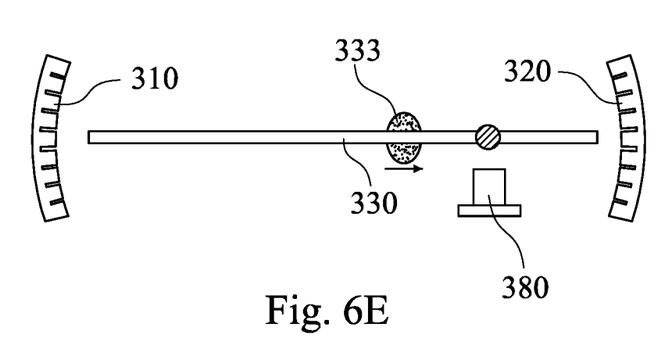
Figure 6F:
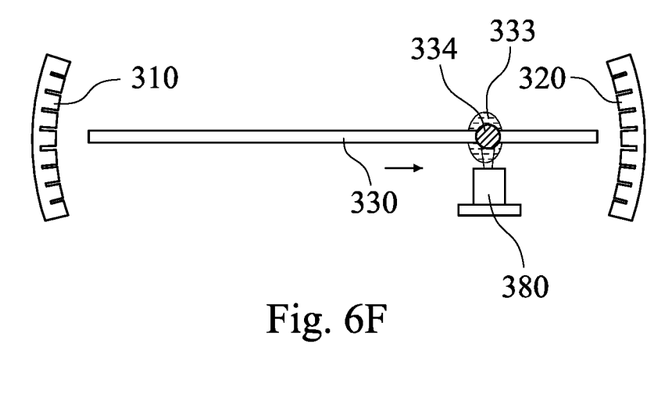

Please refer to FIGS. 6A, 6B, 6C, 6D, 6E and 6F. FIGS. 6A, 6B, 6C, 6D, 6E and 6F are process diagrams of the chemical analysis method by using acoustically actuated droplet 200 as shown in FIG. 3. In the step 220, a leading droplet 331 is provided, as shown in FIG. 6A. The leading droplet 331 is transported to the thread 330 by the first droplet transporter 350a. In the step 230, a leading droplet moving step is performed, as shown in FIG. 6B. An intensity of sound wave of the second sound source 320 is decreased, so that the leading droplet 331 is moved to the second sound source 320. In the step 240, at least one droplet is provided, as shown in FIG. 6C. In FIG. 6C, the number of the at least one droplet is one, that is, a droplet 332 is transported to the thread 330 by the second droplet transporter 350b. In the step 250, a droplet moving step is performed, as shown in FIG. 6D. The droplet 332 and the leading droplet 331 are moved to the second sound source 320. In the step 260, a droplet merging step is performed, as shown in FIG. 6D and FIG. 6E. The droplet 332 and the leading droplet 331 are merged into a testing droplet 333. In the step 270, a detection step is performed, as shown in FIG. 6F. The testing droplet 333 is transported to a detecting region 334, and the detecting region 334 is corresponding to the detection device 380, so as to detect the testing droplet 333.

The details of the aforementioned steps 220 to 270 are described as follows. In the embodiment of FIG. 5 and FIGS. 6A to 6F, the first droplet transporter 350a drives the leading solution in the first solution container 353a by a first peristatic pump 354a, and delivers the leading solution to a first droplet dispenser 352a in a first tubing 351a. The leading droplet 331 is dropped on the thread 330 by the first droplet dispenser 352a. Next, the intensity of sound wave of the second sound source 320 is decreased while the intensity of sound wave of the first sound source 310 is increased, and the resulting sound intensity gradient breaks the equilibrium state of the actuated droplet, so that the leading droplet 331 is moved toward the second sound source 320. Before the leading droplet 331 moves to the position of the second droplet dispenser 350b, the intensity of sound wave of the second sound source 320 is increased while the intensity of sound wave of the first sound source 310 is decreased, so as to maintain the leading droplet 331 at the original position.

Then, the second droplet transporter 350b drives the reagent solution in the second solution container 353b by a second peristatic pump 354b, and delivers the reagent solution to the second droplet dispenser 352b in a second tubing 351b. The droplet 332 is dropped on the thread 330 by the second droplet dispenser 352b. Finally, the intensity of sound wave of the second sound source 320 is decreased while the intensity of sound wave of the first sound source 310 is increased, so that both the leading droplet 331 and droplet 332 can be moved to the second sound source 320. A volume of the leading droplet 331 can be larger than or equal to a volume of the droplet 332, and the volumes of the leading droplet 331 and the droplet 332 can be less than or equal to 5 μL. Preferably, the volumes of the leading droplet 331 and the droplet 332 are not less than 2 μL to prevent excessive droplet shrinkage due to evaporation of solvent.

If the volume of the leading droplet 331 is larger than the volume of the droplet 332, the leading droplet 331 moves farther than the droplet 332, so that the leading droplet 331 will catch the droplet 332 and merge into the testing droplet 333. However, if the volume of the leading droplet 331 is equal to the volume of the droplet 332, both droplets possess identical range of movement, so that the leading droplet 331 can be merged with the droplet 332 into the testing droplet 333. By merging the leading droplet 331 and the droplet 332, the reaction between the sample and the reagent can be triggered.

Furthermore, the detection device 380 is biased toward the second sound source 320, and located on one side of the thread 330. The detection method of the present disclosure can be but is not limited to fluorometry or the absorption spectroscopy. When the detection method is fluorometry, the detection device 380 can include a laser source 381 and a mini-spectrometer 382. The laser source 381 is placed above the thread 330. The mini-spectrometer 382 is placed on the side of the thread 330, and a laser beam emitted from the laser source 381 is orthogonal to the optical axis of the mini-spectrometer 382.

When the testing droplet 333 is transported to the detecting region 334, the testing droplet 333 is irradiated by the laser source 381; the absorption spectrum of the testing droplet 333 is recorded. When the testing droplet 333 in the detecting region 334, the testing droplet 333 movement can be stopped for detection, or detection can be carried out on the fly. After the data acquisition is complete, the intensity of sound wave of the second sound source 320 is adjusted again, so that the detected testing droplet 333 is transported out the detecting region 334.

Therefore, the chemical analysis method by using acoustically actuated droplet guides the droplet by the sound wave suspension technology combined with the thread. Automation of the processes is achieved by implementing electronic microcontrollers, and one can control dispensing the droplets, transport of the droplets, and the data acquisition to achieve the purpose of analyzing microscale liquid samples.

EXAMPLES

Detection 1. Effect of Different pH Values on Fluorescein

Figure 7:
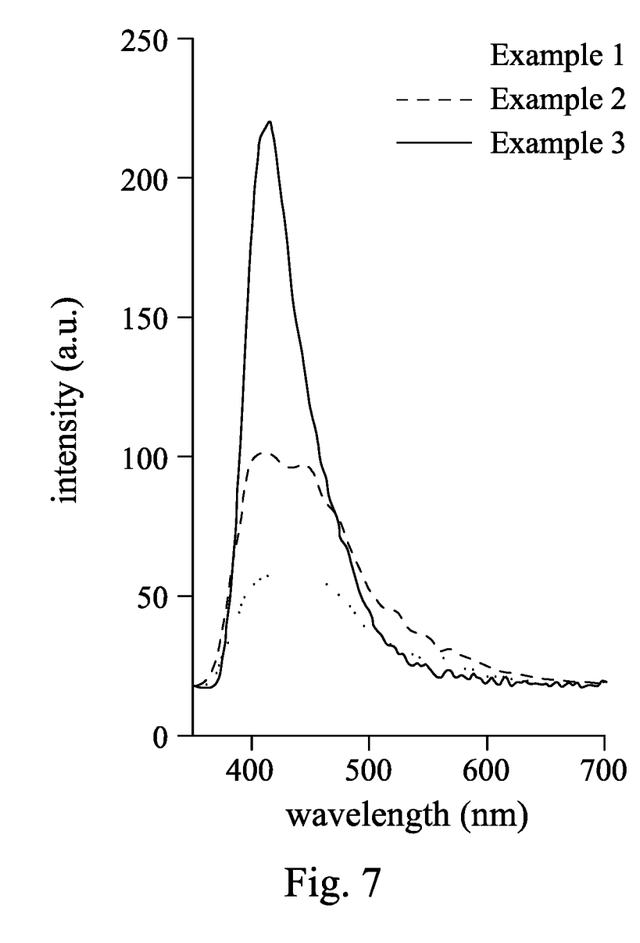
FIG. 7 is a graph of intensity-vs.-wavelength according to Examples 1 to 3 of the present disclosure.

Please refer to FIG. 7, which is a graph of intensity-vs.-wavelength according to Examples 1 to 3 of the present disclosure. In Example 1 to Example 3 of the present disclosure, the fluorescein solution at the concentration of $10^{-6}$ M is the reagent solution, and the leading solution (sample solution) is 0.1 M hydrochloric acid solution, deionized water, or 0.1 M sodium hydroxide solution, respectively. In Example 1 to Example 3, the step 210 to the step 270 are performed to execute the chemical analysis by using acoustically actuated droplet in FIG. 3, wherein the volumes of the transmitted leading droplet and droplet are 3.6 μL.

Fluorescein is a kind of fluorophore, which has different forms of molecules at different pH values. For example, in an alkaline environment, fluorescein loses hydrogen ions, while in an acidic environment, fluorescein obtains hydrogen ions. Therefore, as shown in FIG. 7, after the excitation with the laser beam having an excitation wavelength of 450 nm, the fluorescence intensity at 520 nm of Example 3 is greater than that of Example 1 and Example 2. The result indicates that the fluorescence intensity of fluorescein in the alkaline environment is larger than that in the acidic environment, and can be proved that the device system of the present disclosure can be able to detect the behavior of fluorescence intensity under different pH values.

Detection 2. Assay of Hydrolysis of FITC-Casein

Figure 8:
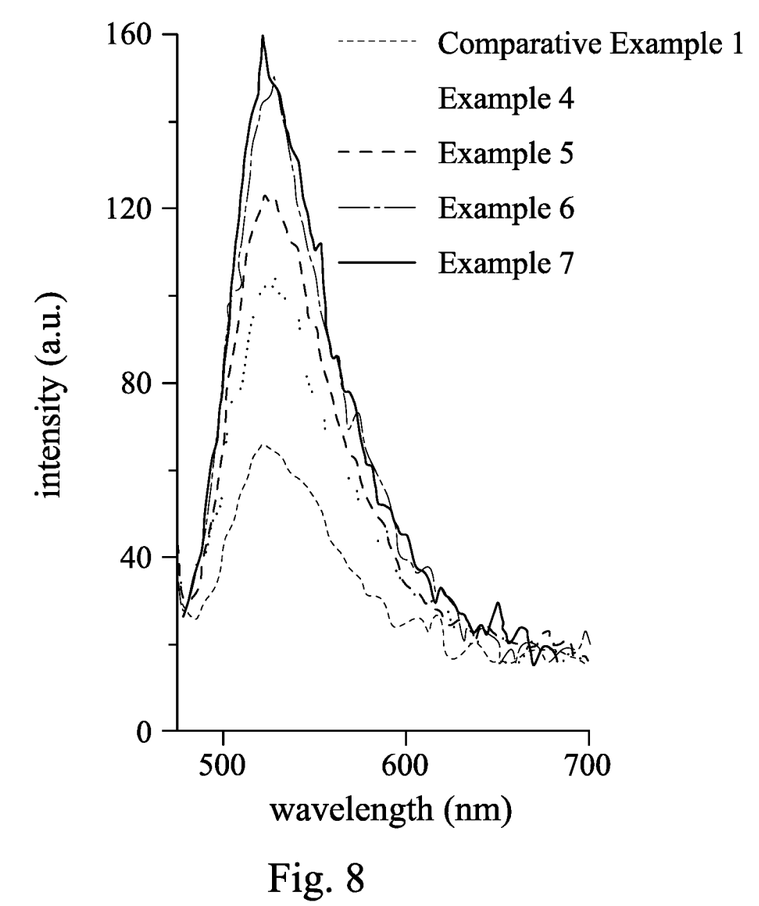
FIG. 8 is a graph of intensity-vs.-wavelength according to Examples 4 to 7 and Comparative Example 1 of the present disclosure.
Figure 9:
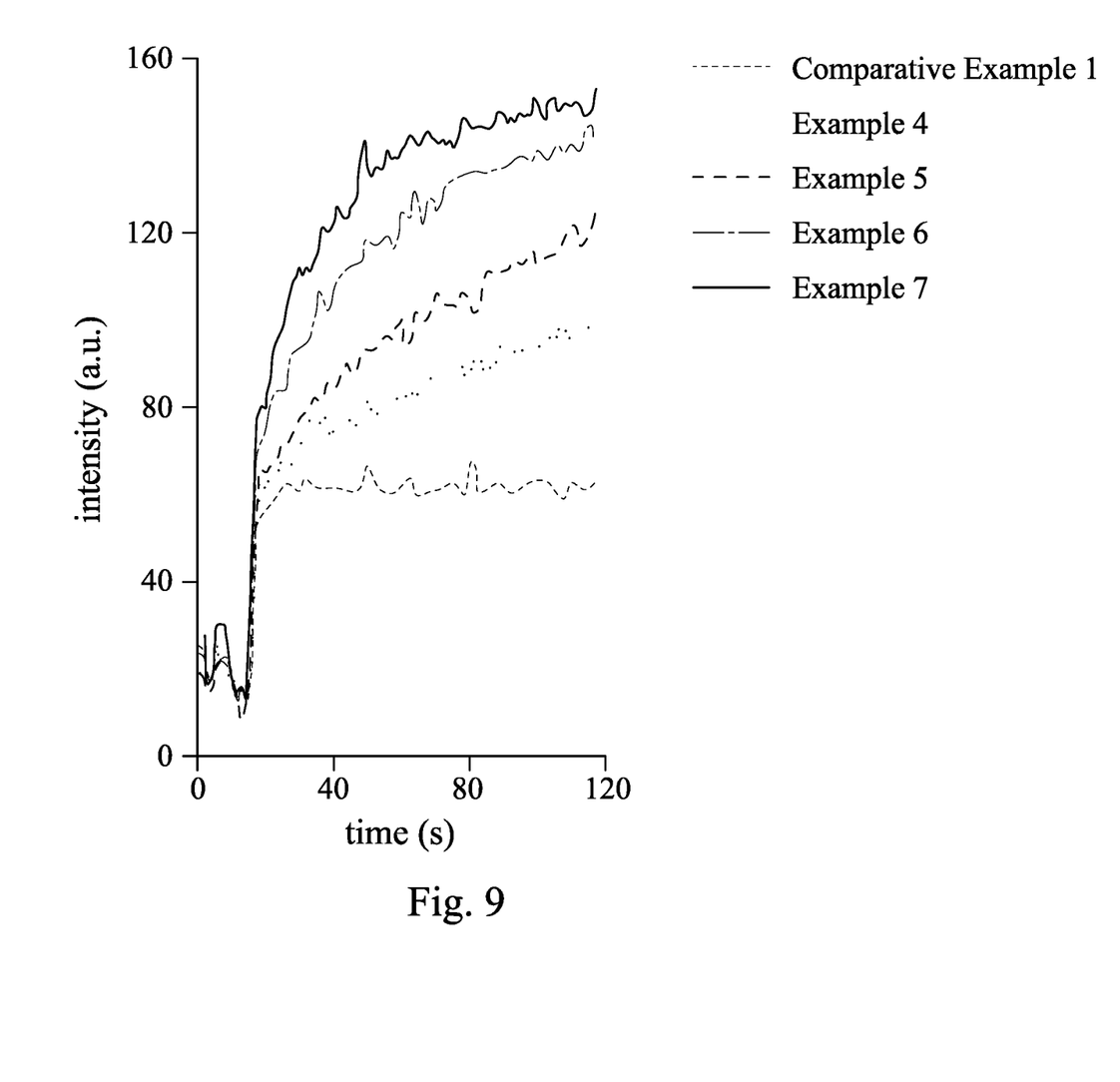
FIG. 9 is a graph of intensity-vs.-time according to Examples 4 to 7 and Comparative Example 1 of the present disclosure.

Please refer to FIG. 8 and FIG. 9. FIG. 8 is a graph of intensity-vs.-wavelength according to Examples 4 to 7 and Comparative Example 1 of the present disclosure. FIG. 9 is a graph of intensity-vs.-time according to Examples 4 to 7 and Comparative Example 1 of the present disclosure. In Example 4 to Example 7 of the present disclosure, the fluorescein isothiocyanate (FTIC)—casein solution (in phosphate buffer, pH=7.3) is the reagent solution at the concentration of $10^{-3}$ mg/mL, and the leading solution (sample solution) is 1244 U/mL, 6220 U/mL, 12443 U/mL, and 62215 U/mL trypsin solution (in phosphate buffer, pH=7.3), respectively. In Comparative Example 1, the FTIC-casein solution (in phosphate buffer, pH=7.3) is the reagent solution at the concentration of $10^{-3}$ mg/mL, and the leading solution (sample solution) is the phosphate buffer without trypsin. In Example 4 to Example 7 and Comparative Example 1, the step 210 to the step 270 are performed to execute the chemical analysis by using acoustically actuated droplet in FIG. 3, wherein the volumes of the transmitted leading droplet and droplet are 3.6 μL.

As shown in FIG. 8, after the excitation with the laser beam having an excitation wavelength of 450 nm, the emission wavelengths of Example 4 to Example 7 and Comparative Example 1 are 520 nm, but the fluorescence intensities in Example 4 to Example 7 are greater than that of Comparative Example 1. This result shows that the device system of the present disclosure is able to monitor the hydrolysis reaction of FTIC-casein via trypsin. Furthermore, as shown in FIG. 9, the merged droplet of FTIC-casein and trypsin reaches the detecting region at 1 second after merging, and the increase of fluorescence intensity in Example 4 to Example 7 indicates that the reaction proceeds within the time of fluorescence measurement.

Detection 3. Assay of β-Galactosidase

Figure 10:
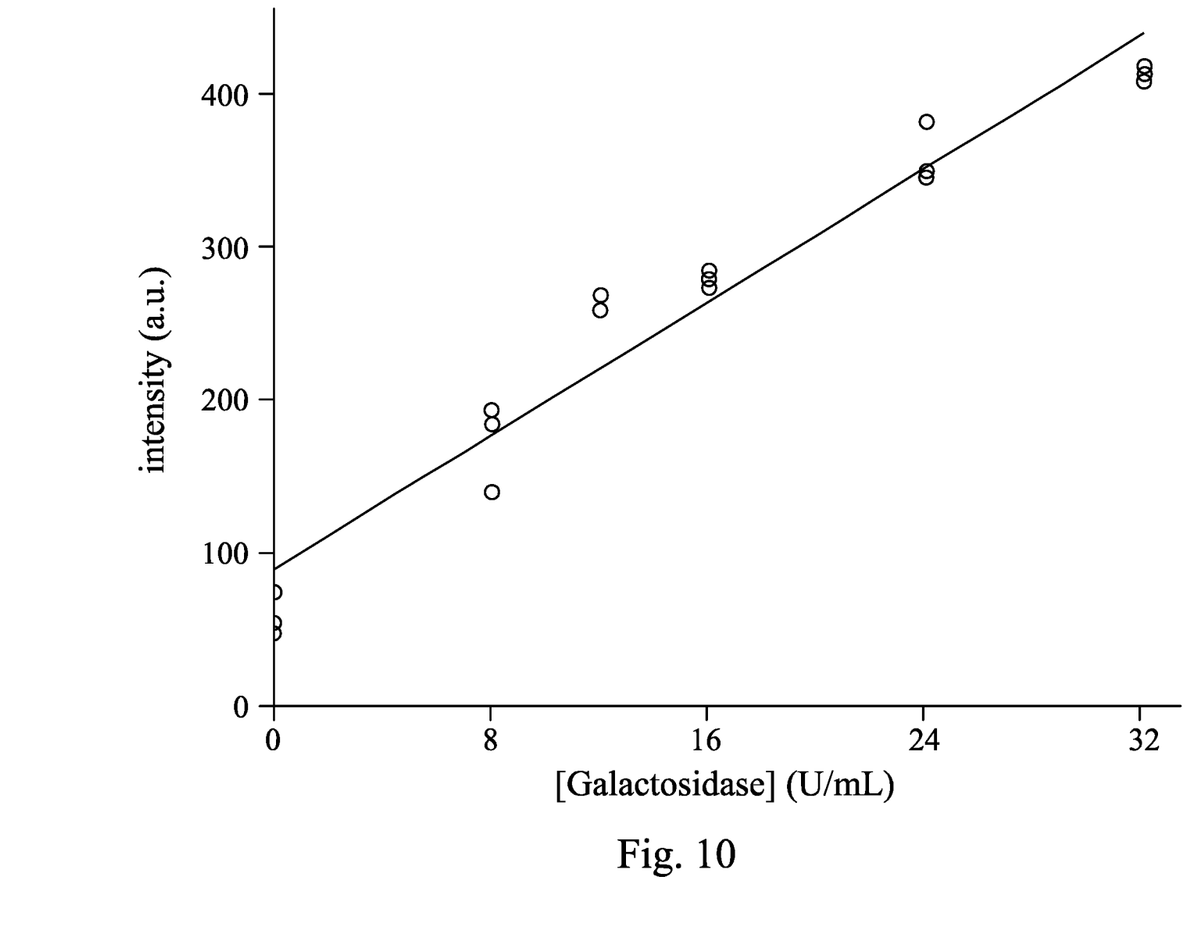
FIG. 10 is a graph of intensity-vs.-activity according to Examples 8 to 13 of the present disclosure.

Please refer to FIG. 10, which is a graph of intensity-vs.-activity according to Examples 8 to 13 of the present disclosure. In Example 8 to Example 13 of the present disclosure, the fluorescein di(β-D-galactopyranoside) (FDG) solution (in phosphate buffer, pH=7.3) is the reagent solution at the concentration of 0.2 mg/mL, and the leading solution (sample solution) is 0 U/mL, 8 U/mL, 12 U/mL, 16 U/mL, 24 U/mL, and 32 U/mL β-galactosidase solution (in phosphate buffer, pH=7.3). In Example 8 to Example 13, the step 210 to the step 270 are performed to demonstrate the chemical analysis by using acoustically actuated droplet in FIG. 3, wherein the volumes of the transmitted leading droplet and droplet are 3.6 μL.

As shown in FIG. 10, when the activity of β-galactosidase is in the range of 0 U/mL to 32 U/mL, the fluorescence intensity is linearly related to the activity of β-galactosidase. This result proves that the device system of the present disclosure can be used to analyze β-galactosidase quantitatively.

The results of the present disclosure indicate that the acoustically actuated droplet apparatus can be able to handle microscale droplets, enable the chemical reaction by merging the droplets, and enable the detection of the reaction products following droplet merger. Therefore, the technique of the present disclosure can be applied to construct an analytical instrument for chemical or biochemical analysis of microliter range liquid samples. This kind of instrument can be utilized in research, industrial, and clinical laboratories.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. An acoustically actuated droplet apparatus, comprising:
   a first sound source comprising a first emitting surface;
   a second sound source comprising a second emitting surface, wherein the second emitting surface and the first emitting surface are arranged opposite to each other;
   a thread coaxially passed through and placed between the first sound source and the second sound source, wherein the thread is hydrophobic;
   two fixed columns connected to two ends of the thread, wherein the first sound source and the second sound source are placed between the two fixed columns; and at least one droplet transporter comprising a tubing, a droplet dispenser and a solution container, wherein the droplet dispenser is connected with the solution container by the tubing, and the droplet dispenser is placed near the thread.

2. The acoustically actuated droplet apparatus of claim 1, wherein the first emitting surface and the second emitting surface are concave structures.

3. The acoustically actuated droplet apparatus of claim 2, wherein the first emitting surface and the second emitting surface are provided with a plurality of sound transducers, and the sound transducers are arranged in an array.

4. The acoustically actuated droplet apparatus of claim 1, further comprising:
an extension spring connected between one end of the thread and one of the two fixed columns.

5. The acoustically actuated droplet apparatus of claim 1, wherein the thread is made of a chemically inert hydrophobic material.

6. The acoustically actuated droplet apparatus of claim 1, wherein the at least one droplet transporter further comprises a peristatic pump, the tubing is connected to the solution container via the peristatic pump, and the peristatic pump is for driving the solution in the solution container to the droplet dispenser.

\* \* \* \* \*